United States Patent
Yarden et al.

(10) Patent No.: US 11,249,013 B2
(45) Date of Patent: Feb. 15, 2022

(54) TESTING QUALITY AND POTENCY OF PLANT MATERIAL

(71) Applicant: Gemmacert Ltd., Raanana (IL)

(72) Inventors: Dana Yarden, Tel Aviv (IL); Roni Attali, Hod Hasharon (IL); Menachem Kaplan, Tel Aviv (IL); Oded Shoseyov, Shoham (IL); Amit Ruf, Hod Hasharon (IL)

(73) Assignee: Gemmacert Ltd., Raanana (IL)

( * ) Notice: Subject to any disclaimer, the term of this patent is extended or adjusted under 35 U.S.C. 154(b) by 454 days.

(21) Appl. No.: 16/464,380

(22) PCT Filed: Jan. 31, 2019

(86) PCT No.: PCT/US2019/015941
§ 371 (c)(1),
(2) Date: May 28, 2019

(87) PCT Pub. No.: WO2019/152578
PCT Pub. Date: Aug. 8, 2019

(65) Prior Publication Data

US 2020/0333242 A1    Oct. 22, 2020

Related U.S. Application Data

(60) Provisional application No. 62/786,456, filed on Dec. 30, 2018, provisional application No. 62/760,055, (Continued)

(51) Int. Cl.
*G01J 3/28* (2006.01)
*G01N 21/27* (2006.01)
(Continued)

(52) U.S. Cl.
CPC .......... *G01N 21/274* (2013.01); *G01N 21/01* (2013.01); *G01N 21/31* (2013.01);
(Continued)

(58) Field of Classification Search
CPC .... G01J 3/02; G01J 3/28; G01J 3/2803; G01J 3/10; G01J 3/2823
(Continued)

(56) References Cited

U.S. PATENT DOCUMENTS

| | | |
|---|---|---|
| 2005/0180608 A1 | 8/2005 | Tanabata |
| 2011/0222060 A1 | 9/2011 | Smith |

(Continued)

FOREIGN PATENT DOCUMENTS

WO    2017/134669    8/2017

OTHER PUBLICATIONS

PCT Search Report PCT/US2019/015941, dated May 2, 2019.

*Primary Examiner* — Md M Rahman
(74) *Attorney, Agent, or Firm* — Dekel Patent Ltd.; David Klein

(57) ABSTRACT

A device for holding and testing plant material includes a sample container including a sample fixation member for affixing thereto a plant sample such that the plant sample is held vertically in the sample container, a test and calibration reference, a spectrometer arranged to perform spectrometric analysis of the plant sample with respect to spectrometric analysis of the test and calibration reference, and a multiple-degree-of-freedom positioning device configured to cause relative movement between the sample container and the spectrometer.

15 Claims, 4 Drawing Sheets

Related U.S. Application Data filed on Nov. 13, 2018, provisional application No. 62/625,916, filed on Feb. 2, 2018.

(51) Int. Cl.
  *G01N 21/01* (2006.01)
  *G01N 21/31* (2006.01)
  *G01N 33/00* (2006.01)
  *G01N 21/84* (2006.01)

(52) U.S. Cl.
  CPC . *G01N 33/0098* (2013.01); *G01N 2021/0112* (2013.01); *G01N 2021/8466* (2013.01)

(58) Field of Classification Search
  USPC .......................................................... 356/326
  See application file for complete search history.

(56) References Cited

U.S. PATENT DOCUMENTS

| | | |
|---|---|---|
| 2016/0011225 A1 | 1/2016 | Theranos |
| 2016/0139055 A1 | 5/2016 | Pierce, III et al. |

TESTING QUALITY AND POTENCY OF PLANT MATERIAL

FIELD OF THE INVENTION

The present invention generally relates to methods for testing quality and potency of plant material, such as cannabis.

BACKGROUND OF THE INVENTION

PCT Application WO 2017/134669 describes a system and method for determining a quality measure of a plant material, particularly cannabis. The system includes an optical inspection unit that optically inspects one or more regions of the plant material and generates measured image data and spectroscopic data of the regions of the plant material. A control unit includes an analyzer for receiving the measured image data and the measured spectroscopic data of the regions of the plant material. The control unit analyzes the measured image data to determine one or more structural parameters of the plant material, and determines one or more quality measures of the plant material based on a relation between the measured spectroscopic data and the structural parameters.

However, optical analysis of plant material, and especially cannabis, presents several challenges to analytical equipment. One problem is that examined samples tend to be sticky and can contaminate or pollute the sensor lens. Cannabis buds are particularly sticky, since a large fraction of bud volume and weight are trichomes, composed mostly of resin.

Another problem is that examined samples produce fallout, which can pollute the sensor lens and clog components of the equipment. Cannabis buds produce plenty of fallout because they are dried to a very low level of moisture to avoid molding and to extend shelf life. The drying process makes the buds lose any elasticity and weaken their structure, thereby increasing fallout.

Another problem is that examined samples are often very non-homogeneous, because the distribution of the active ingredients can vary in the sample by a substantial percentage. Over 90% of cannabis active ingredients are contained in trichomes of the cannabis bud. The cannabinoids phytocannabinoid tetrahydrocannabinol (THC) and cannabidiol (CBD) are the major active ingredients, being the analgesic compounds of cannabis. The distribution of these active ingredients can be very non-homogeneous.

Another problem is that examined samples most often present varying sizes and irregular shapes. These challenge optical analysis because the results are very sensitive to distance. Furthermore, the varying and irregular sizes can result in the spectrometer sensor missing some of the sample.

SUMMARY OF THE INVENTION

The present invention seeks to provide devices and methods that further improve the system and methods described in PCT Application WO 2017/134669, as described in detail below. The present invention solves the abovementioned problems of the prior art, as is described below.

In one aspect of the invention, the samples are held vertically in the examination device. For example, the sample may be vertically suspended, such as by being held by a grip or threaded on a pin. The sensor or sensors observe the sample horizontally, thus preventing any fallout polluting the sensor lenses.

In another aspect of the invention, the examination device has a hollow bottom so that any sample fallout from the vertically-held sample will fall freely and accumulate in a detachable device base, which can be emptied periodically. For example, the device base may be magnetically attached to the device body, thereby facilitating easy removal and reattachment after emptying.

In another aspect of the invention, a camera cooperates with the spectrometer. The camera identifies the examined sample size and shape in order to select desired sample locations for optical measurement, thereby placing the sensor at a desired distance from the sample surface. This also facilitates keeping sensor lenses void of pollution, as they never come in physical contact with sample.

In another aspect of the invention, a multiple-degree-of-freedom (e.g., 3-axes motion) system manipulates or moves the sensors so they are positioned at desired distances from the desired analyzed sample locations.

In another aspect of the invention, the optical analysis is integrated into an automated sorting line. In the prior art, an automated sorting line presents throughput-related challenges. Lab-style analysis with a single sensor is tolerant to prolonged duration, since in any case much of the time is spent in human action. However, commercial feasibility of automated sorting mandates analysis conclusions within seconds or fractions of seconds, and this is not feasible with a single sensor.

As opposed to the prior art, analysis may be concluded faster by employing a few sensors in either serial or parallel configurations. For example, in a serial configuration, specimens are analyzed in a serial manner, one after the other. Analysis is accelerated by placing few sensors along the line, each examining a different area of the analyzed specimen. In a parallel configuration, specimens are analyzed concurrently, each by one or more dedicated sensors.

There is thus provided in accordance with an embodiment of the invention a device for holding and testing plant material including a sample container including a sample fixation member for affixing thereto a plant sample such that the plant sample is held vertically in the sample container, a test and calibration reference, a spectrometer arranged to perform spectrometric analysis of the plant sample with respect to spectrometric analysis of the test and calibration reference, and a multiple-degree-of-freedom positioning device configured to cause relative movement between the sample container and the spectrometer.

In an embodiment of the invention, dynamic spectroscopic measurements may be taken to improve accuracy. Rather than predefining how many measurements must be taken to achieve a desired accuracy, in this embodiment, the user may input or modify the number of measurements to be taken or the system may automatically determine how many samples must be taken and at which locations on the sample in order to achieve the desired accuracy.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
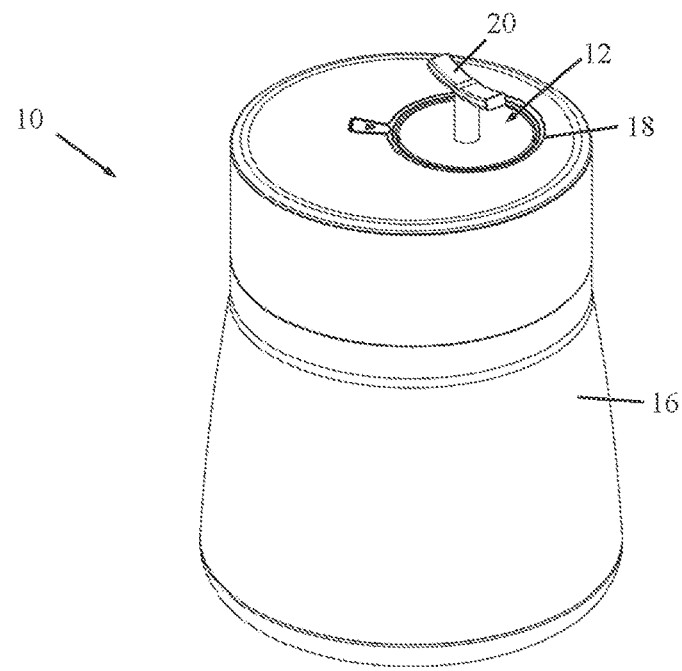
FIG. 1 is a simplified perspective illustration of a device for holding and testing plant material, constructed and operative in accordance with a non-limiting embodiment of the present invention.
Figure 2:
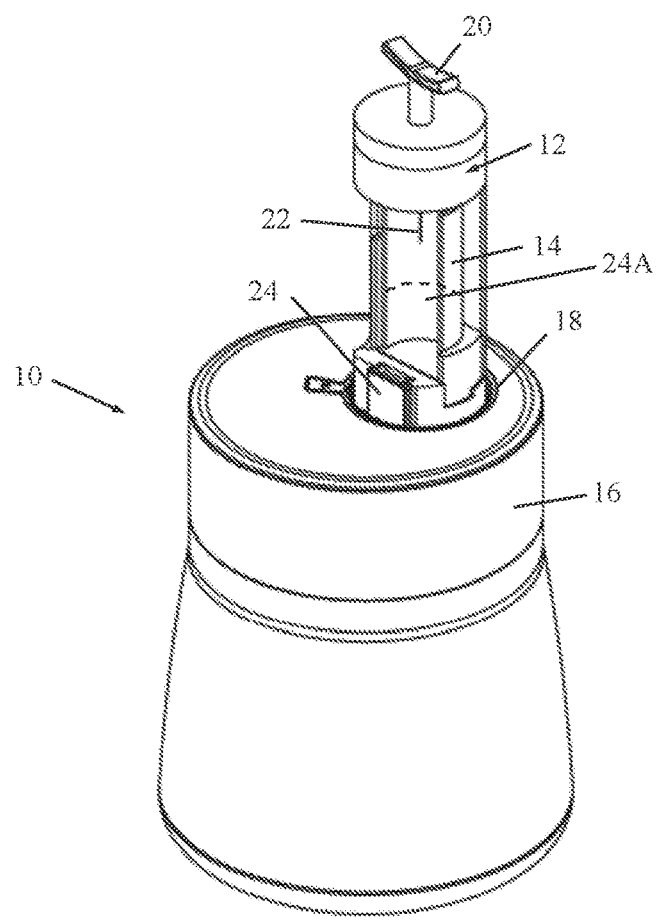
FIG. 2 is a simplified perspective illustration of the device for holding and testing plant material, showing the sample container partially removed from the housing.

Reference is now made to FIGS. 1-2, which illustrate a device 10 for holding and testing plant material, such as but not limited to, cannabis, constructed and operative in accordance with a non-limiting embodiment of the present invention.

Device 10 includes a sample container 12, which may include a reflector 14, such as but not limited to, a gold or gold-plated mirror disposed in sample container 12; both the reflector and the sample container may be cylindrical or other shapes. In the illustrated embodiment, sample container 12 is inserted in a housing 16 through an opening 18. Sample container has an upper handle 20 for grasping sample container 12 to pull it out from the housing 16 and insert it back and for rotating the analyzed sample as needed.

A sample fixation member 22, such as but not limited to a pin, is disposed in sample container 12 for affixing thereto a plant sample. In the illustrated embodiment, the sample fixation member 22 protrudes downwards from the upper portion of sample container 12. In alternative embodiments, the sample fixation member 22 may be positioned in other places, as long as it does not interfere with analysis of the sample.

Device 10 includes a test and calibration reference 24, which may be disposed in sample container 12, such as at the bottom of the container 12.

Figure 3:
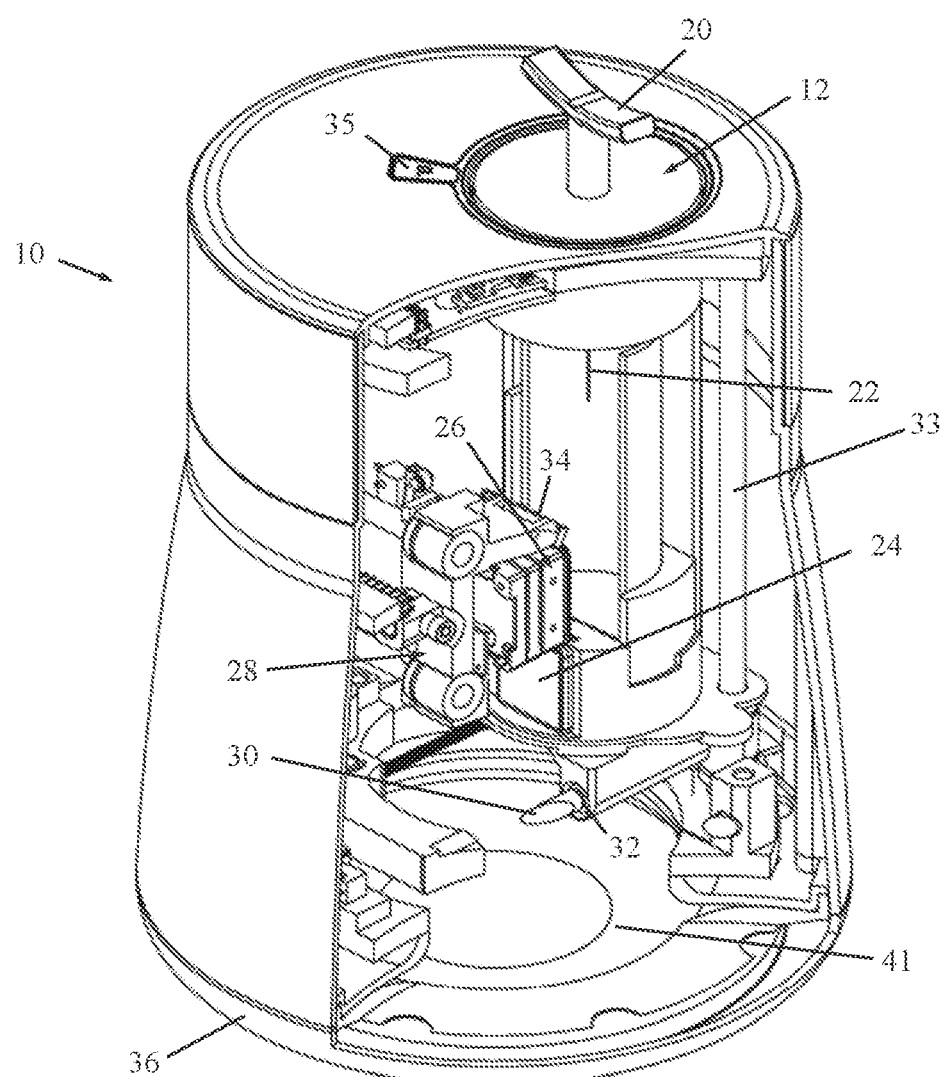
FIG. 3 is a simplified cutaway illustration of the device for holding and testing plant material.

Reference is now made to FIG. 3. Device 10 includes a spectrometer 26 for analyzing the samples. Every spectrometer must be calibrated periodically; typical periods range between once a day and once for every analyzed sample. In the prior art, calibration may be accomplished by pointing the spectrometer at an "ideal white" calibration reference. For most spectrometers it is a manual user action. Generally the more often spectrometer is calibrated, the more accurate subsequent analysis results. Spectrometer 26 may include a processor for processing and analyzing the data sensed by spectrometer 26; alternatively, the processor may be separate but in communication with spectrometer 26.

As opposed to the prior art, in the invention, test and calibration reference 24 is integrated in device 10 and is used to do calibration before every analysis, automatically, without need for a user action. This improves analysis accuracy. The test and calibration reference 24 may have a known and defined color (e.g., white) and spectrometric properties.

The spectrometer 26 is mounted on a multiple-degree-of-freedom positioning device 28, such as but not limited to, an X-Y-Z positioner, for translation and/or rotation of the spectrometer 26 to view the sample at any orientation. A locking device 30, such as a locking bar (shown cutaway in the drawing) that can be moved to a locking position with a receptacle 32, may be used to lock the sample container 12 with respect to the spectrometer 26 so that the sample does not move during the spectrometric analysis. When not locked, sample container 12 can move along rail or rails 33. The locking bar of the locking device 30 may be an integral part of the positioning device 28 and receptacle 32 may be at the bottom of the sample container 12.

Alternatively, the sample container 12 may be coupled to the multiple-degree-of-freedom positioning device 28 so that the sample container 12 is moved relative to the stationary spectrometer 26. In general, the multiple-degree-of-freedom positioning device 28 causes relative movement between the sample container 12 and the spectrometer 26: the sample container 12 may be stationary and the spectrometer 26 may move; the sample container 12 may move and the spectrometer 26 may be stationary; or both the sample container 12 and the spectrometer 26 may be moved by the multiple-degree-of-freedom positioning device 28.

Accordingly, in one aspect of the invention, the samples are held vertically in the examination device 10 and the spectrometer 26 or other examination sensor or sensors observe the sample horizontally, thus preventing any fallout polluting the sensor lenses.

Figure 6:
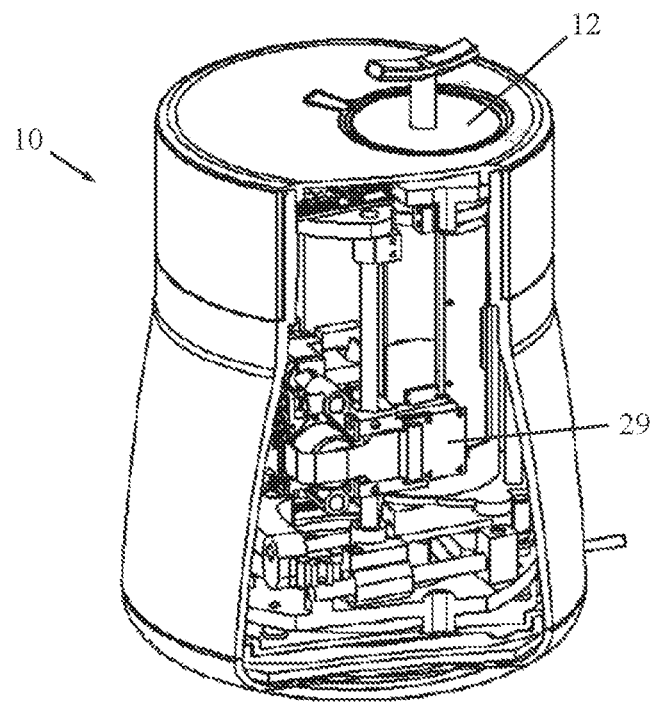
FIG. 6 is another cutaway illustration of the device for holding and testing plant material, showing a camera that cooperates with the spectrometer.

A camera 29 (FIG. 6) may cooperate with the spectrometer 26 and with the multiple-degree-of-freedom positioning device 28. Camera 29 may identify the examined sample size and shape in order to select desired sample locations for optical measurement, thereby commanding the multiple-degree-of-freedom positioning device 28 to position the sensor (spectrometer 26) at a desired distance from the sample surface. This also facilitates keeping sensor lenses void of pollution, as they never come in physical contact with sample. Camera 29 may be separate from spectrometer 26 or may be provided as an integral unit with spectrometer 26.

Device 10 includes a light source 34 (e.g., LEDs) that illuminates the plant sample, such as for viewing by the camera. A control button 35 may be provided for controlling one or more operations of the device.

The reflector 14 is positioned behind the analyzed flower (or other plant part) to increase the potential of light interaction with target molecules. Some of the light from light source 34 is reflected directly by the flower, whereas some of the light crosses the flower and reflects off a surface behind the flower and traverses the flower once again, thus increasing the potential of interaction. Reflector 14 is preferably a concave reflector, which has superior accuracy over a flat reflector. The concave shape encloses the bud effects, since some of the light first impinges on the reflector sides and gets reflected onto the sides of the bud, thus increasing the potential of light interaction with target molecules. This helps dealing with sparse and/or very thin flowers, for which plain reflectance has been proven inadequate. The concave reflector improves thick flower analysis results as well.

The spectrometer 26 first analyzes the test and calibration reference 24 to establish the current reference for analyzing the plant sample as a calibration before every analysis. Thus, spectrometer 26 performs spectrometric analysis of the plant material with respect to spectrometric analysis of the test and calibration reference 24.

Cannabis active ingredients are not distributed evenly across the bud. This presents a problem in variability of the analysis results when exposing various sides of the bud to the spectrometer. The invention solves this problem by exposing various sides of the bud by rotating the bud by rotation of sample fixation member 22. Rotation may not be used all the time, because there is a trade-off between analysis duration and results accuracy.

The device 10 can perform analysis of distinct substances. In the case of cannabis, for example, three or more distinct substances may be analyzed, such as intact buds, extract and round cannabis matter. Device 10 is designed in modular manner, so that various sample and testing holders may be easily inserted and removed. These include, without limitation, pin or grip for various bud structures, reflectors, extract cuvette holder, ground matter holder and the final test and calibration reference (described below).

Figure 7:
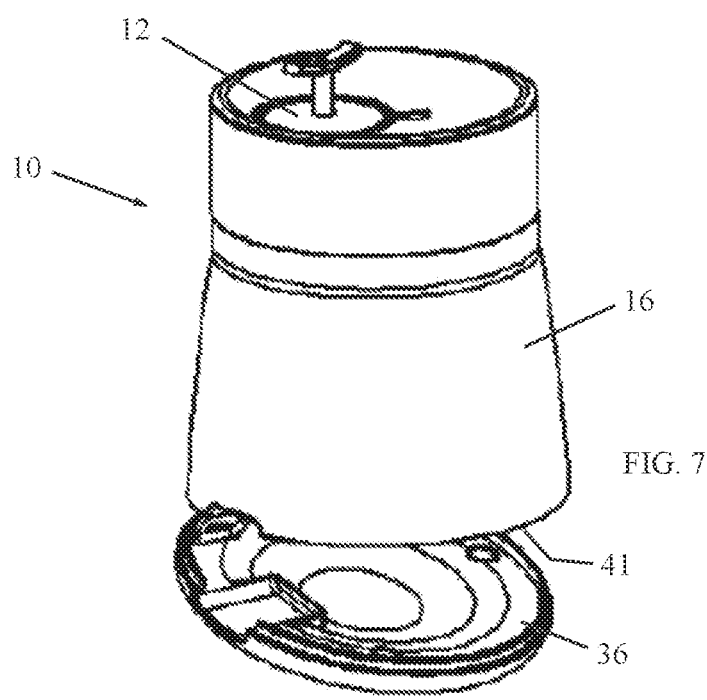
FIG. 7 is a simplified perspective illustration of a removable base of the device.

Pieces of analyzed cannabis buds inevitably fall off and gradually accumulate within the device. Device 10 is designed to allow easy emptying of this accumulated debris. For example, device 10 has a hollow bottom 41 (FIGS. 3 and 7) so that any sample fallout from the vertically-held sample will fall freely and accumulate in a detachable device base 36, which can be emptied periodically. For example, the device base 36, may be held onto housing 16 by strong magnets, yet is easily detachable from housing 16 by applying moderate force. Debris accumulates in the base 36. The user needs only to lift housing 16 from base 36 and turn base 36 over to dispose the debris.

The spectrometer lens may be polluted over time. Housing 16 may be lifted from base 36 to empty the debris and to gain access to clean the spectrometer lens, such as with an alcohol wipe. The lens may be accessible through an opening at the body bottom.

Final testing of any assembled device may last considerable time, which is a problem for mass production in which time is critical. In the prior art, mass production involves concurrent testing of many units. This has the disadvantage of heavy investment in dedicated test equipment for testing many devices at the same time. Use of dedicated test equipment has another disadvantage of extra space in the manufacturing area.

Figure 4A:
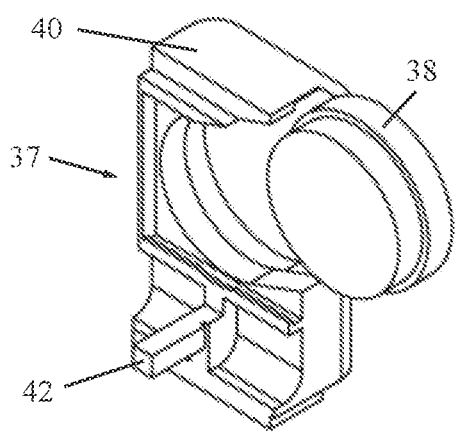
FIGS. 4A and 4B are simplified perspective illustrations of a final assembly calibration module, in accordance with a non-limiting embodiment of the present invention, with a calibration disc during and after insertion in a holder, respectively.
Figure 4B:
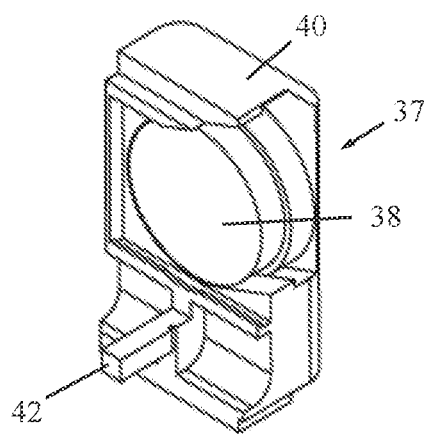

As opposed to the prior art, the invention includes a final test and calibration unit 37, which is now described with reference to FIG. 4.

The final test and calibration unit 37 includes a test and calibration reference disc 38 which may have a known and defined color (e.g., white) and spectrometric properties. Reference disc 38 may be held in a calibration holder 40. The entire calibration holder 40 with reference disc 38 may be inserted through opening 18 into housing 16 (FIGS. 1-2) instead of reflector 14 or sample holders for extract and ground matter analyses. The final test and calibration unit 37 is placed into the device 10 at the end of manufacturing device 10 for final calibration of the spectrometer 26.

The final test and calibration unit 37 may also include a mechanical calibration member 42, such as a bar with a reference pixel or marking, for calibration of pixel-to-millimeter ratio of the visible camera. The final test and calibration unit 37 also serves as a test of positioning device 28 by locating certain marks on 40 in the visible image.

One advantage of the final test and calibration unit 37 of the invention is that no dedicated test equipment is needed. Instead, testing is entirely self-contained in the device. The test and calibration reference unit 37 is disposed in the device 10 and includes visible indications (mechanical calibration member 42) for camera calibration and rare earth piece (test and calibration reference disc 38) for spectrometer calibration. Motion system functionality and accuracy of the device may be verified by analyzing camera images.

In this manner, the sole external equipment needed is a processor or computer which can process and analyze multiple samples simultaneously.

Individual spectrometers, including identical model devices manufactured in the same batch, differ in various attributes including their respective signal-to-noise ratios. The invention solves this problem by measuring signal-to-noise ratios after assembly of the devices, and if needed, applying algorithmic compensation. This allows grading the devices and tailoring them for different markets with different specifications.

Signal-to-noise is measured by analyzing multiple spectra of the rare earth embedded in the final test and calibration reference. These spectra are captured over a duration of time; this accounts for thermal changes.

As noted above, individual spectrometers of same model and even same batch differ. However, they must deliver practically identical analysis results (within an acceptable tolerance). To this end individual spectrometer characteristics must be learned and subsequently serve correction to transform their spectra into a common "nominal" base prior to using that spectra for analysis.

Cross-device calibration may be accomplished by analyzing and comparing multiple spectra of the rare earth embedded in the test and calibration reference, captured by various spectrometers.

It is noted that there is another challenge in testing plant material with a spectrometer. Currently, compact and low-cost spectrometers do not exhibit wavelength stability over time. As a result, the spectra of a particular sample measured at different times by the same spectrometer may be shifted, such as by a few nanometers higher or lower. Laboratory spectrometers can achieve wavelength stability by a combination of closed-loop control and cooled detector.

However, in some embodiments, the test and calibration reference 24 may not be capable of detecting any such shift because reflectance spectra measured off test and calibration reference 24 may either change due to combined effects of illumination changes and spectrometer wavelength instability, and/or may be void of peaks which could enable wavelength shift detection.

In an embodiment of the invention, a solution is provided for this problem with test and calibration reference 24, as is now described.

An additional wavelength reference 24A (shown in broken lines in FIG. 2) may be embedded in the device which features at least one clear peak in its spectra. This peak is measured at different times at varying wavelengths, thus allowing measurement of the spectrum shift.

The two references (24 and 24A) allow separating the effects of illumination and wavelength instability over time: test and calibration reference 24 serves exclusively illumination measurement and the additional introduced wavelength reference 24A serves exclusively wavelength stability.

The additional wavelength reference 24A may be implemented by a small piece of PET (polyethylene terephthalate) attached to the lower part of the reflector 14. PET features a steep spectrum peak at 1663 nm. It is a low-cost widely used polymer and PET decays only when exposed to intense light or high temperatures, neither of which happen within the device.

Thus, this solution allows employing inherently unstable spectrometer designs, and yet compensates for the instability by the addition of a very low cost wavelength reference.

Figure 5:
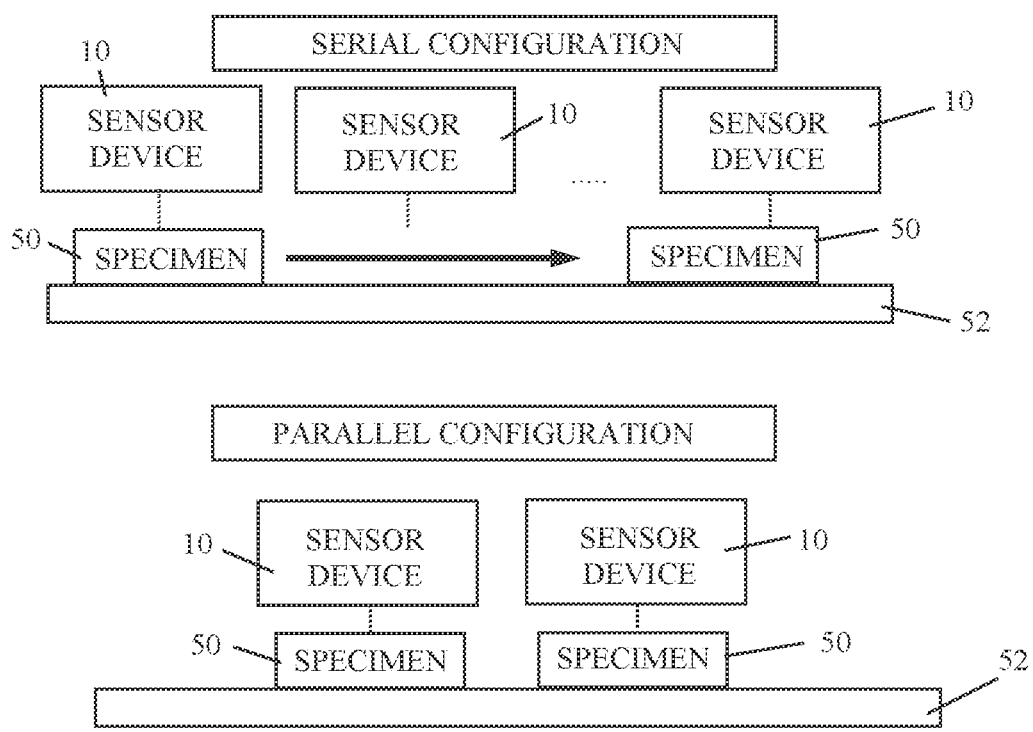
FIG. 5 is a simplified block diagram of optical analysis integrated into an automated sorting line, in accordance with a non-limiting embodiment of the present invention.

Reference is now made to FIG. 5, which is a simplified block diagram of optical analysis integrated into an automated sorting line, in accordance with a non-limiting embodiment of the present invention.

In another aspect of the invention, the optical analysis is integrated into an automated sorting line. As opposed to the prior art, analysis may be concluded faster by employing a few sensors in either serial or parallel configurations. For example, in a serial configuration, specimens 50 are analyzed in a serial manner, one after the other, on a conveyor 52 that conveys the samples to each examination device 10. Analysis is accelerated by placing several sensors along the conveyor 52, each examining a different area of the analyzed specimen. In a parallel configuration, specimens 50 are analyzed concurrently, each by one or more dedicated sensor devices 10. (In the parallel configuration, the conveyor moves in and out of the drawing page; in the serial configuration, the conveyor moves to the left and right of the drawing page.)

The two alternatives (serial and parallel) are functionally equivalent, and choosing between them depends primarily on physical space limitations. Serial configuration results in a longer line whereas parallel configuration results in shorter yet wider line. Serial configuration slightly simplifies sorting line mechanics, featuring less ejection mechanisms, one per sorting category.

What is claimed is:

1. A device for holding and testing plant material comprising:
   a sample container comprising a sample fixation member for affixing thereto a plant sample such that said plant sample is held vertically in said sample container;
   a test and calibration reference;
   a spectrometer arranged to perform spectrometric analysis of said plant sample with respect to spectrometric analysis of said test and calibration reference; and
   a multiple-degree-of-freedom positioning device configured to cause relative movement between said sample container and said spectrometer.

2. The device according to claim 1, further comprising a light source configured to illuminate said plant sample.

3. The device according to claim 2, further comprising a reflector positioned behind said plant sample, wherein a portion of light from said light source is reflected directly by said plant sample, another portion of the light traverses said plant sample and reflects off said reflector and traverses said plant sample once again.

4. The device according to claim 3, further comprising a housing with an opening through which said sample container and said reflector are insertable and removable.

5. The device according to claim 3, wherein said reflector is concave.

6. The device according to claim 1, further comprising a locking device configured to lock said sample container with respect to said spectrometer.

7. The device according to claim 1, further comprising a camera in operative communication with said spectrometer and said multiple-degree-of-freedom positioning device.

8. The device according to claim 7, wherein said camera is configured to command said multiple-degree-of-freedom positioning device to adjust a distance from said spectrometer to said plant sample.

9. The device according to claim 7, wherein said camera is configured to identify an examined sample size and shape and select desired sample orientations of said spectrometer with respect to said plant sample.

10. The device according to claim 7, further comprising a final test and calibration unit that comprises visible indications for camera calibration and a rare earth piece for spectrometer calibration.

11. The device according to claim 1, further comprising a housing in which said sample container is disposed, said housing comprising a detachable device base arranged to receive any debris from said plant sample.

12. The device according to claim 1, further comprising an additional wavelength reference that has at least one clear peak in its spectra, said at least one peak being measurable at different times at varying wavelengths.

13. The device according to claim 1, wherein said sample container comprises a plurality of sample containers and said spectrometer comprises a plurality of spectrometers, and further comprising an automated sorting line with a conveyor for conveying said sample containers to said spectrometers.

14. The device according to claim 13, wherein said conveyor conveys said sample containers to said spectrometers in a serial manner.

15. The device according to claim 13, wherein said conveyor conveys said sample containers to said spectrometers in a parallel manner.

* * * * *